United States Patent [19]
Baumlin et al.

[11] Patent Number: 5,824,887
[45] Date of Patent: Oct. 20, 1998

[54] METHOD AND DEVICE FOR MEASURING THE SURFACE TENSION OF A LIQUID COMPOSITION IN A CURTAIN

[75] Inventors: Jean-Marie Baumlin, Chalon sur Saone; Ghislaine Wywial, Demigny; Nathalie Hautier, Dijon, all of France

[73] Assignee: Eastman Kodak Company, Rochester, N.Y.

[21] Appl. No.: 734,166

[22] Filed: Oct. 21, 1996

[30]     Foreign Application Priority Data

Nov. 22, 1995 [FR]  France ................................... 95 14270

[51] Int. Cl.⁶ .................................................... G01N 13/02
[52] U.S. Cl. ............................................................. 73/64.48
[58] Field of Search ............................................ 73/64.48

[56]          References Cited
          FOREIGN PATENT DOCUMENTS 3-20640   1/1991   Japan ..................................... 73/64.43

OTHER PUBLICATIONS

"Waves in a viscous liquid curtain" by S.P. Lin and G. Roberts, Mar. 17, 1981, pp. 443–458, Journal of Fluid Mechanics (1981 vol. 112).

*Primary Examiner*—Hezron E. Williams
*Assistant Examiner*—Daniel S. Larkin
*Attorney, Agent, or Firm*—Susan L. Parulski

[57]          ABSTRACT

The invention relates to the measurement of the dynamic surface tension of a liquid, particularly a liquid forming a curtain. The measuring device includes introducing, into the curtain, an obstacle adapted to create a standing wave defining two inverted Vs. A light source illuminates the standing wave and a camera forms an image of at least part of the standing wave. The light source or obstacle is adjusted such that the two inverted Vs are substantially identical, and the surface tension is determined.

13 Claims, 5 Drawing Sheets

METHOD AND DEVICE FOR MEASURING THE SURFACE TENSION OF A LIQUID COMPOSITION IN A CURTAIN

FIELD OF THE INVENTION

The invention concerns a method and apparatus for measuring the dynamic surface tension of a liquid composition flowing in the form of a substantially vertical curtain, and concerns in particular the measurement of the dynamic surface tension of photographic compositions.

BACKGROUND OF THE INVENTION

Typically, a curtain coating machine comprises a feed system from which a photographic composition flows in the form of at least one layer. By way of example, the feed system includes one or more slots from which flow a plurality of layers which are superimposed on a slightly inclined flow plane before reaching a lip at which the liquid composition leaves the coating device to form a substantially vertical curtain and be deposited on a moving support, driven for example by means of a suitable cylinder.

There exist various methods for measuring the surface tension of the liquid in the curtain. Amongst the best known, the one known as "Mach angle measurement" will be cited, consisting of introducing a rod with a diameter of 0.32 cm into the curtain, so as to disturb the curtain by creating a standing wave in the form of an inverted V (with respect to the direction of flow in the curtain. Then the angle between the tangent at any point on the standing wave is measured with respect to the vertical, directly from a photograph of the wave, or using a projection of the photograph onto a screen. The principle of the measurement is illustrated in FIG. 1. The liquid is maintained in the form of a curtain 9 by means of edge guides 2, 3. An obstacle 11 is introduced into the curtain so as to disturb it. The point of introduction of the obstacle coincides substantially with the apex of the inverted V 5 formed by the standing wave produced by the obstacle. From the angle θ, Lin's equation is used to derive therefrom the surface tension whose expression is as follows:

$$\sigma = \frac{\rho Q \sin^2 \theta}{2}$$

in which:

σ is the surface tension of the liquid;

Q is the flow per unit width (cm²/s);

U is the local velocity of the liquid (cm/s); and

θ is the angle between the straight line portions defining the V with respect to the axis of symmetry of the V (i.e. the vertical).

Such a technique is described by way of example in the article entitled "*Waves in a viscous liquid curtain*" by S. P. Lin and G. Roberts, Journal of Fluid Mechanics (1981, vol 112, pp 443–458). According to the approach described in this document, the curtain is disturbed so as either to break it locally (no liquid inside the V) or to modify its flow plane locally without breaking it.

The main drawback of such a measurement method relates to the fact that the measurement has substantial imprecision, related principally to the difficulty in measuring the angle. This imprecision is particularly great when the measurement is performed without breaking the curtain.

The solution consisting of performing the measurement by breaking the curtain, even if it offers greater precision, is not completely satisfactory in that it does not make it possible to apprehend certain phenomena, notably with regard to the diffusion of surfactants in a multilayer system.

The patent application JP-A-3-20640 filed in the name of FUJI PHOTO FILMS CO Ltd and entitled "*Method and apparatus for measuring surface tension*" describes an approach similar to the previous one, breaking the curtain by the combined action of an obstacle with low wettability, introduced into the curtain, and a suitably configured air jet. The limitations of such a technique were mentioned previously.

SUMMARY OF THE INVENTION

Thus one of the objects of the present invention is to provide a method and a device for measuring dynamic surface tension which do not present the above-mentioned drawbacks.

Other objects will appear in detail in the following description. These objects are achieved according to the present invention by means of a method of measuring the dynamic surface tension of a liquid composition flowing in the form of a substantially vertical curtain, comprising the following steps:

a) introducing into the curtain an obstacle able to disturb the flow plane of the curtain locally by creating a standing wave forming a V which is inverted with respect to the direction of flow and whose apex coincides substantially with the point of introduction of the obstacle into the curtain;

b) illuminating the standing wave by means of at least one source of light radiation;

c) recovering the radiation reflected by the wave so as to form a light image of at least part of the wave, the image defining at least a portion of two Vs which are inverted with respect to the direction of flow, having their axes of symmetry aligned, and offset in the direction of flow;

d) adjusting the position of the radiation source and/or of the obstacle so that the Vs have their corresponding portions substantially parallel, and;

e) determining the surface tension of the liquid in the flow from a measurement of the angle formed by the straight-line portions defining the two inverted Vs with respect to their axes of symmetry.

Advantageously, the reflected radiation is recovered by means of a CCD camera of the type having a CCD sensor matrix network.

Advantageously also, the standing wave is illuminated by means of two light sources disposed on each side of the optical axis of the camera.

By way of example, the obstacle used to disturb the curtain is in the form of a rod whose end forms an angle of 30° to 60° with respect to the axis of the rod.

Advantageously also, the determination of the surface tension comprises the following steps:

a) digitally processing the image in order to obtain a digital representation of the two inverted Vs;

b) calculating the angle formed by each of the four straight-line portions forming the two inverted Vs with respect to their axes of symmetry;

c) calculating a mean value of the angles; and d) calculating the corresponding surface tension from said mean value.

According to the present invention, a device is also produced for measuring the dynamic surface tension of a liquid composition flowing in the form of a substantially vertical curtain, comprising:

a) means for introducing into the curtain an obstacle able to disturb the flow plane of the curtain locally by creating a standing wave forming a V which is inverted with respect to the direction of flow and whose apex coincides substantially with the point of introduction of the obstacle into the curtain;

b) means for illuminating the standing wave by means of at least one source of light radiation;

c) means for recovering the radiation reflected by the wave so as to form a light image of at least part of the wave, the image defining at least a portion of two Vs which are inverted with respect to the direction of flow, having their axes of symmetry aligned, and offset in the direction of flow;

d) means for adjusting the position of the radiation source and/or of the obstacle so that the Vs have their corresponding portions substantially parallel; and e) means for determining the surface tension of the liquid composition in the flow from a measurement of the angle formed by the straight-line portions defining the two inverted Vs with respect to their axes of symmetry.

BRIEF DESCRIPTION OF THE DRAWINGS

In the following description, reference will be made to the drawings in which.

DESCRIPTION OF THE PREFERRED EMBODIMENT

Figure 1:
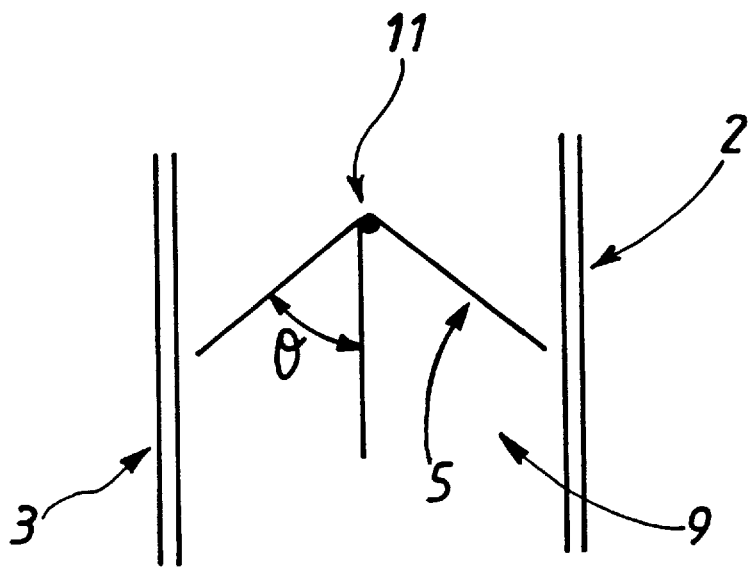
FIG. 1 illustrates diagrammatically the principle of the measurement according to the so-called "Mach angle measurement" technique.
Figure 2:
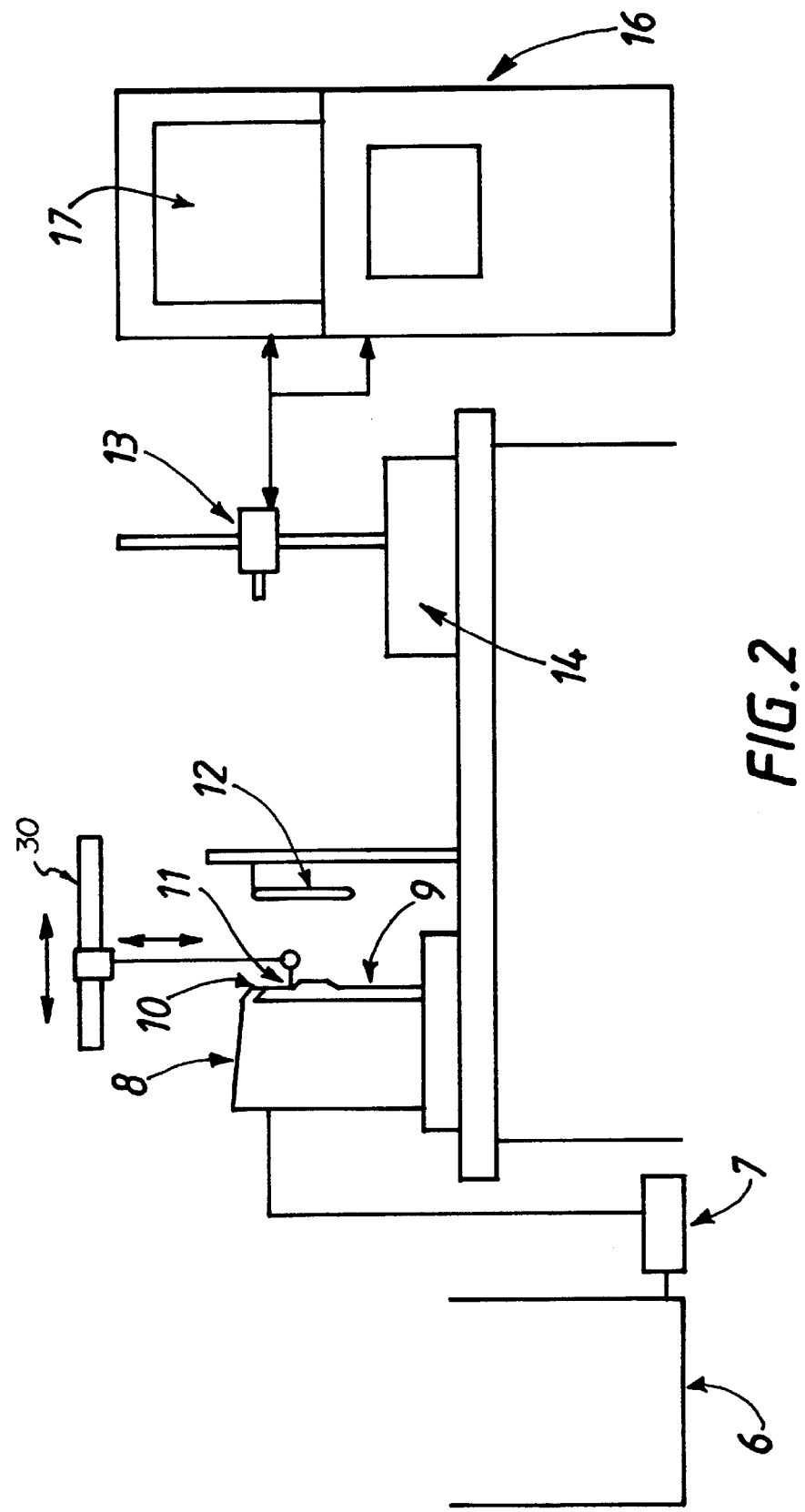
FIG. 2 depicts an embodiment of the device according to the present invention.

FIG. 2, to which reference is now made, illustrates diagrammatically an advantageous embodiment of the device according to the invention. As can be seen from FIG. 2, a liquid composition contained in a tank 6 is pumped continuously by means of a pump 7 so as to feed a coating device 8. The liquid composition leaves the coating device at a lip 10 in order to form a substantially vertical curtain 9. Into the curtain 9, a member 11 is introduced, designed to disturb the curtain by creating a standing wave which will be the subject of a detailed description subsequently. According to the embodiment depicted, the obstacle 11 is disposed in front of the curtain. According to another possible embodiment, the obstacle is disposed at the rear of the curtain so as not to interfere with the photographing by the camera 13. The member 11 is mounted on a mounting member 30 so that its position in the curtain can be adjusted, both in vertical and horizontal directions. The device according to the invention also comprises illumination means 12 disposed so that the standing wave created by the member 11 can be illuminated in order to form an image thereof at least partially on a matrix network of CCD sensors of a camera 13, whose position (in the direction of width of the curtain and in the direction of the height) can also be adjusted as desired (carriage 14). The camera 13 is connected to a control unit 16 (PC type) and to a display unit 17 for displaying the digital image of the chosen curtain portion.

As mentioned with reference to the Mach angle measurement technique, the obstacle 11 is designed so that its introduction into the curtain creates a standing wave defining an inverted V whose apex coincides substantially with the point of introduction of the member 11.

Figure 3:
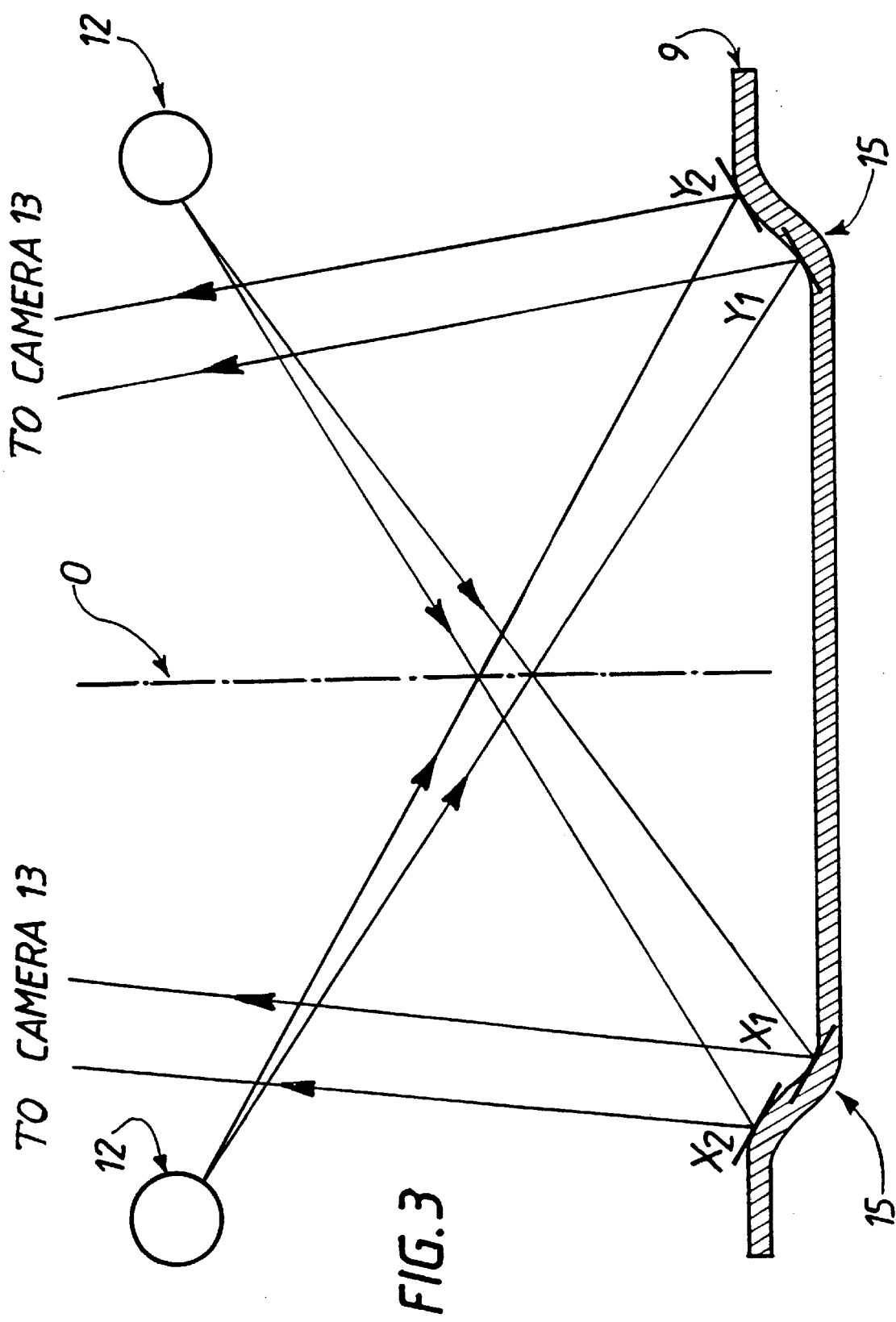
FIG. 3 illustrates diagrammatically a transverse section of the curtain at the level of the standing wave together with the illumination of the wave in order to form an image thereof in accordance with that in FIG. 4.

A transverse section (at the axis X, FIG. 4) through the standing wave is depicted diagrammatically in FIG. 3. As can be seen clearly, the disturbance results in a change in the flow plane of the curtain 9 within the inverted V. The section depicted in FIG. 3 is produced at a distance Z (FIG. 4) from the point of introduction of the obstacle 11 into the curtain.

Figure 4:
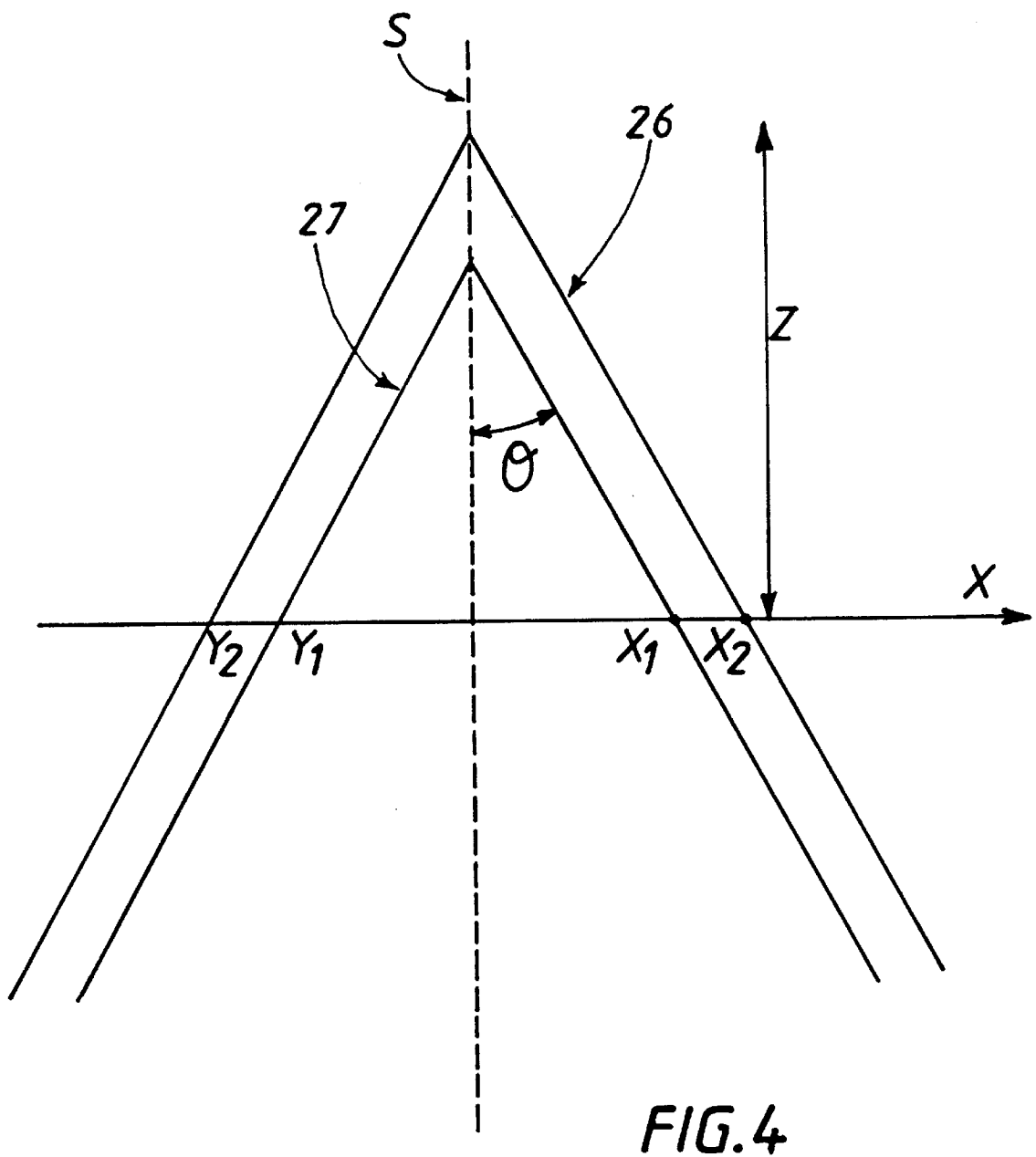
FIG. 4 depicts an image of the standing wave according to the invention.

By illuminating this area of the curtain in the manner depicted in FIG. 3, by means of two neon lights 12 for example, situated on each side of the optical axis (O) of the camera 13, an image of the type depicted in FIG. 4 is formed.

As mentioned previously, the image of the standing wave 15 defines two clear inverted Vs 26, 27. According to one alternative, only a portion of each of the two Vs is displayed, the portion displayed preferably being substantially the same for the two Vs. The Vs (or portions of Vs) are offset in the direction of flow of the curtain (arrow Z) and aligned along their axis of symmetry S. According to the present invention, the respective position of the illumination means and/or of the obstacle 11 is adjusted (manually or controlled by the computer 16) so that the two inverted Vs are substantially identical, that is to say so that they have their respective corresponding straight-line portions substantially parallel. When the adjustment is made manually, the operator uses the monitoring screen 17 to display the respective position of the Vs 26, 27.

The image thus formed is stored by means of a CCD camera 13 connected to a computer 16, which, according to a preferred embodiment, performs a digital processing of at least part of the image of the wave. By way of indication, using a linear regression, the computer assimilates the respective portions of the Vs 26, 27 to straight-line portions and determines the angle $\theta$ formed by the straight-line portions forming the two Vs with respect to the vertical, that is to say with respect to the axis of symmetry of the Vs 26, 27. Advantageously, the computer produces a mean value of the four angles calculated and uses this mean angle in the Lin equation to calculate the surface tension of the liquid. Advantageously, the processing software VISILOG® sold by NOESIS® is used. This method of processing the image is given only as an example.

According to one embodiment, the speed of flow of the liquid is determined by a measurement consisting of recording the distance travelled by a particle (or air bubble) present in the curtain over a given time.

Figure 5:
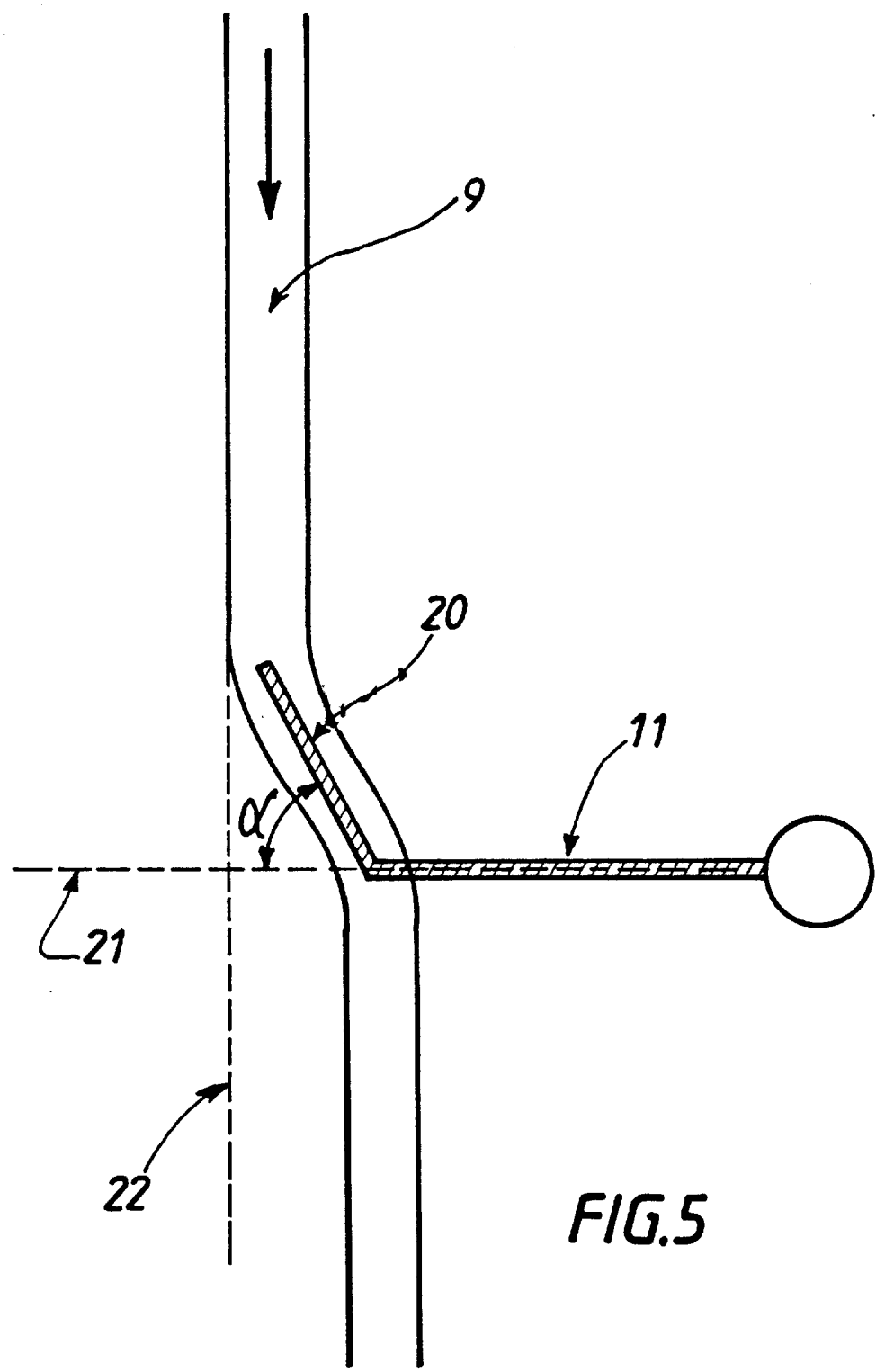
FIG. 5 illustrates a preferred embodiment of an obstacle used to disturb the liquid curtain according to the invention.

FIG. 5 depicts an advantageous embodiment of an obstacle 11 which can be used according to the invention to disturb the curtain 9. According to this advantageous embodiment, the obstacle 11 is in the form of a rod 11, the end 20 of which forms an angle $\alpha$ with respect to the axis 21 of the rod which, by way of example, can vary between 30° and 60°. As can be seen in FIG. 5, the curtain flows along the end part 20 of the rod, thus creating a localised modification of the flow plane 22 of the curtain 9 without causing any break in the flow of the liquid. Obviously, this form is given only by way of example and other forms can be used for implementing the method according to the invention.

With certain adjustments, notably in the calculation of the surface tension, the invention could be applied in the same way by applying a disturbance suitable for causing a break in the flow of the curtain.

The invention which has been described is advantageous in that it allows a measurement, both precise and automatic, of a surface tension of a liquid composition in a flow in the form of a curtain. As mentioned previously, the invention is particularly suited to measuring the surface tension of a photographic composition.

In the above description, reference was made to particularly advantageous embodiments. It is evident that variations can be made thereto without departing from the spirit of the invention as claimed hereinafter.

What is claimed is:

1. Method of measuring the dynamic surface tension of a liquid composition flowing in the form of a substantially vertical curtain, comprising the following steps:
   a) introducing into the curtain an obstacle able to disturb the flow plane of the curtain locally by creating a standing wave forming a V which is inverted with respect to the direction of flow and whose apex coincides substantially with the point of introduction of the obstacle into the curtain;
   b) illuminating the standing wave by means of at least one source of light radiation;
   c) recovering the radiation reflected by the wave so as to form a light image of at least part of the wave, the image defining at least a portion of two Vs which are inverted with respect to the direction of flow, having their axes of symmetry aligned, and offset in the direction of flow;
   d) adjusting the position of the radiation source and/or of the obstacle so that the Vs have their corresponding portions substantially parallel; and
   e) determining the surface tension of the liquid in the flow from a measurement of the angle θ formed by the straight-line portions defining the two inverted Vs with respect to their axes of symmetry.

2. Method according to claim 1, characterized in that the reflected radiation is recovered by means of a CCD camera of the matrix CCD type.

3. Method according to claim 2, characterized in that the standing wave is illuminated by means of two light sources disposed on each side of the optical axis of the camera.

4. Method according to claim 1, characterized in that the obstacle is in the form of a rod whose end forms an angle of 30° to 60° with respect to the axis of the rod.

5. Method according to claim 1, characterized in that the determination of the surface tension comprises the following steps:
   a) digitally processing the image in order to obtain a digital representation of the two inverted Vs;
   b) calculating the angle θ formed by each of the four straight-line portions forming the two inverted Vs with respect to their axes of symmetry;
   c) calculating a mean value of the angles; and
   d) calculating the corresponding surface tension from the mean value.

6. Method according to claim 1, characterized in that the liquid composition is a photographic composition.

7. Device for measuring the dynamic surface tension σ of a liquid composition flowing in the form of a substantially vertical curtain, comprising:
   a) means for introducing into the curtain an obstacle able to disturb the flow plane of the curtain locally by creating a standing wave forming a V which is inverted with respect to the direction of flow and whose apex coincides substantially with the point of introduction of the obstacle into the curtain;
   b) a source of light radiation for illuminating the standing wave;
   c) means for recovering the radiation reflected by the wave so as to form a light image of at least part of the wave, the image defining at least a portion of two Vs which are inverted with respect to the direction of flow, having their axes of symmetry aligned, and offset in the direction of flow;
   d) means for adjusting the position of the radiation source and/or of the obstacle so that the Vs have their corresponding portions substantially parallel; and
   e) means for determining the surface tension of the liquid composition in the flow from a measurement of the angle θ formed by the straight-line portions defining the two inverted Vs with respect to their axes of symmetry.

8. Device according to claim 7, characterized in that the means for recovering the reflected radiation comprise a camera of the matrix CCD type.

9. Device according to claim 8, characterized in that the illumination means comprise two light sources disposed on each side of the optical axis of the camera.

10. Device according to claim 7, characterized in that the obstacle comprises a rod whose end forms an angle of 30° to 60° with respect to the axis of the rod.

11. Device according to claim 7, characterized in that the means for determining the surface tension comprise:
   a) means for digitally processing the image in order to obtain a digital representation of the two inverted Vs;
   b) means for calculating the angle formed by each of the four straight-line portions forming the two inverted Vs with respect to their axes of symmetry;
   c) means for producing a mean value of the angles; and
   d) means for calculating the corresponding surface tension from the mean value.

12. An apparatus for measuring the dynamic surface tension of a liquid flowing in the form of a curtain, the apparatus comprising:
   an obstacle disposed in the curtain disturbing the flow plane and creating a standing wave forming a V which is inverted with respect to the direction of flow, the apex of the inverted V coinciding substantially with the point of disposal of the obstacle into the curtain;
   a light source illuminating the standing wave;
   an image forming member recovering the light reflected by the wave to form a light image of at least part of the wave, the image defining at least a portion of two Vs which are inverted with respect to the direction of flow, having their axes of symmetry aligned and offset in the direction of flow;
   a mounting member for adjusting the position of the light source and/or the obstacle such that the inverted Vs have their corresponding portions substantially parallel; and
   a computer for determining the surface tension of the liquid composition in the flow from a measurement of the angle formed by the straight-line portions defining the two inverted Vs with respect to their axes of symmetry.

13. A method of measuring the dynamic surface tension of a liquid flowing in the form of a curtain, the method comprising the steps of:
   positioning an obstacle into the curtain to disturb the flow plane of the curtain and creating a standing wave forming a V which is inverted with respect to the direction of flow, the apex of the inverted V coinciding substantially with the point of positioning of the obstacle into the curtain;

illuminating the standing wave;

forming a light image of at least part of the wave, the image defining at least a portion of two Vs which are inverted with respect to the direction of flow, having their axes of symmetry aligned, and offset in the direction of flow;

adjusting the position of the illumination source and/or of the obstacle so that the Vs have their corresponding portions substantially parallel; and determining the surface tension of the liquid in the flow from a measurement of the angle formed by the straight-line portions defining the two inverted Vs with respect to their axes of symmetry.

* * * * *